US011039867B2

(12) United States Patent
Bohay et al.

(10) Patent No.: US 11,039,867 B2
(45) Date of Patent: Jun. 22, 2021

(54) CALCANEAL BONE PLATE TARGETING GUIDE

(71) Applicant: Biomet C.V., Warsaw, IN (US)

(72) Inventors: Donald Bohay, Ada, MI (US); John G Anderson, Lowell, IN (US); John Early, Dallas, TX (US); Leslie Grujic, Sydney (AU); Ross Takkwong Leung, Bridgewater, NJ (US); Chris Bremer, Warsaw, IN (US); Kelly Lackey, Warsaw, IN (US)

(73) Assignee: Biomet C.V., Warsaw, IN (US)

( * ) Notice: Subject to any disclaimer, the term of this patent is extended or adjusted under 35 U.S.C. 154(b) by 291 days.

(21) Appl. No.: 16/255,349

(22) Filed: Jan. 23, 2019

(65) Prior Publication Data

US 2019/0150999 A1 May 23, 2019

Related U.S. Application Data

(63) Continuation of application No. 14/458,901, filed on Aug. 13, 2014, now abandoned.

(51) Int. Cl.
*A61B 17/80* (2006.01)
*A61B 17/17* (2006.01)

(52) U.S. Cl.
CPC ...... *A61B 17/8061* (2013.01); *A61B 17/1728* (2013.01); *A61B 17/808* (2013.01)

(58) Field of Classification Search
CPC .............. A61B 17/1728; A61B 17/808; A61B 17/1725; A61B 17/80; A61B 17/68; A61B 17/746; A61B 2002/30777
See application file for complete search history.

(56) References Cited

U.S. PATENT DOCUMENTS

| 2006/0116679 | A1 | 6/2006 | Lutz et al. |
| 2006/0264946 | A1* | 11/2006 | Young ................ A61B 17/8052 606/915 |
| 2007/0055253 | A1 | 3/2007 | Orbay et al. |
| 2008/0234749 | A1 | 9/2008 | Forstein |
| 2009/0118769 | A1 | 5/2009 | Sixto, Jr. et al. |
| 2009/0125069 | A1* | 5/2009 | Sixto, Jr. ............ A61B 17/8047 606/286 |

(Continued)

OTHER PUBLICATIONS

"U.S. Appl. No. 14/458,901, Advisory Action dated Mar. 20, 2018", 4 pgs.

(Continued)

*Primary Examiner* — Samuel S Hanna
(74) *Attorney, Agent, or Firm* — Schwegman Lundberg & Woessner, P.A.

(57) ABSTRACT

A calcaneal targeting device includes a guide body configured to target a corresponding calcaneal bone plate. The guide body includes at least one mounting opening that is configured to align with a corresponding mounting opening of the calcaneal bone plate, at least one targeting opening configured to align with a corresponding fixation opening of the calcaneal bone plate, and a guiding portion that includes a tali targeting opening and a first elongated opening that has a first length. The first elongated opening is configured to allow sliding of a guide wire across the first length and align the tali targeting opening with a sustentaculum tali.

18 Claims, 7 Drawing Sheets

(56) References Cited

U.S. PATENT DOCUMENTS

| | | |
|---|---|---|
| 2011/0218576 A1 | 9/2011 | Galm et al. |
| 2013/0211459 A1 | 8/2013 | Horan et al. |
| 2014/0066996 A1 | 3/2014 | Price et al. |
| 2015/0157337 A1* | 6/2015 | Wolf .................. A61B 17/1721 606/96 |
| 2016/0045238 A1 | 2/2016 | Bohay et al. |

OTHER PUBLICATIONS

"U.S. Appl. No. 14/458,901, Examiner Interview Summary dated Aug. 6, 2018", 3 pgs.

"U.S. Appl. No. 14/458,901, Examiner Interview Summary dated Aug. 31, 2017", 3 pgs.

"U.S. Appl. No. 14/458,901, Examiner Interview Summary dated Dec. 11, 2018", 5 pgs.

"U.S. Appl. No. 14/458,901, Final Office Action dated Jan. 5, 2018", 14 pgs.

"U.S. Appl. No. 14/458,901, Final Office Action dated Jan. 7, 2019", 19 pgs.

"U.S. Appl. No. 14/458,901, Non Final Office Action dated Feb. 22, 2017", 10 pgs.

"U.S. Appl. No. 14/458,901, Non Final Office Action dated Jun. 29, 2018", 17 pgs.

"U.S. Appl. No. 14/458,901, Notice of Non-Compliant Amendment dated Oct. 9, 2018", 4 pgs.

"U.S. Appl. No. 14/458,901, Response filed Jan. 19, 2017 to Restriction Requirement dated Dec. 21, 2016", 6 pgs.

"U.S. Appl. No. 14/458,901, Response filed Mar. 5, 2018 to Final Office Action dated Jan. 5, 2018", 11 pgs.

"U.S. Appl. No. 14/458,901, Response filed Mar. 23, 2018 to Advisory Action dated Mar. 20, 2018", 10 pgs.

"U.S. Appl. No. 14/458,901, Response filed May 17, 2017 to Non Final Office Action dated Feb. 22, 2017", 10 pgs.

"U.S. Appl. No. 14/458,901, Response filed Aug. 22, 2018 to Non Final Office Action dated Jun. 29, 2018", 12 pgs.

"U.S. Appl. No. 14/458,901, Response filed Oct. 23, 2017 to Notice of Non-Compliant Amendment dated Jun. 21, 2017", 8 pgs.

"U.S. Appl. No. 14/458,901, Response filed Dec. 10, 2018 to Notice of Non-Compliant Amendment dated Oct. 9, 2018", 11 pgs.

"U.S. Appl. No. 14/458,901, Restriction Requirement dated Dec. 21, 2016", 8 pgs.

Gitajn, MD, et al., "Assessing Accuracy of Sustentaculum Screw Placement During Calcaneal Fixation", American Orthopaedic Foot & Ankle Society, 282-286.

U.S. Appl. No. 14/458,901, filed Aug. 13, 2014, Calcaneal Bone Plate Targeting Guide.

U.S. Appl. No. 15/681,908, filed Aug. 21, 2017, Calcaneal Bone Plate Targeting Guide.

* cited by examiner

CALCANEAL BONE PLATE TARGETING GUIDE

BACKGROUND OF THE INVENTION

1. Field of the Invention

The present invention relates to surgical devices, and, more particularly, to orthopaedic targeting guides.

2. Description of the Related Art

Calcaneal fractures are a fracture of the calcaneus bone, which is the largest of the tarsal bones and also known as the heelbone. While accounting for a small percentage of total fractures in human patients, calcaneal fractures are the most common type of tarsal bone fracture. The calcaneus is rather large, and most calcaneal fractures occur in healthy persons following a large amount of trauma. Such trauma can result from a person falling a large distance and landing on their feet or during an automobile crash.

When the calcaneus is fractured, there are a few treatment options available. For minor fractures, it can be sufficient to isolate the fractured calcaneus from bearing weight and allowing the calcaneus to heal naturally. For more serious fractures, especially when the calcaneus fragments, installing a bone plate to the calcaneus that also connects to the fragments can compress the fragments to the rest of the calcaneus and provide better healing. When fixating a bone plate to the calcaneus, it is useful if a fixating screw that holds the bone plate to the calcaneus is advanced into relatively dense bone that can provide good fixation of the bone plate.

One bone plate and technique of installing the bone plate to the calcaneus is taught by U.S. Patent Application Publication No. 2014/0066996 (Price et al.). The bone plate taught by Price et al. is implanted onto the calcaneus using a sinus tarsi approach. The bone plate includes an anterior section that has two locking screw holes, an s-shaped posterior facet section having four locking holes which rounds toward the bone at both the inferior and superior edges and is reinforced at the superior edge, and a blade shaped posterior portion having three linearly aligned locking holes and terminating in a tapered portion. Price et al. also teaches a drill guide that connects to the bone plate and that can be used as a handle to guide the bone plate and allow locking screws to be implanted percutaneously to fixate the bone plate to the calcaneus.

One shortcoming of the bone plate and associated targeting drill guide of Price et al. is that if the surgeon wants to attach the bone plate to the calcaneus with a fixation screw in dense bone, the surgeon must determine where there is dense bone and place the bone plate "free hand" to get proper alignment of the bone plate with the dense bone. A free hand placement is when the surgeon moves the bone plate around the calcaneus without any guidance and, usually, multiple fluoroscopic images are taken to get the correct placement of the bone plate relative to the dense bone. This can lead to the surgeon requiring extra time in the operating room to properly align the bone plate and more fluoroscopic images which increase the cost of the procedure and radiation exposure to the patient and surgical team.

What is needed in the art is an easier way to align a bone plate with a calcaneus so that the bone plate is fixated with a bone screw that advances into dense bone.

SUMMARY OF THE INVENTION

The present invention provides a targeting guide that has a tali targeting opening and one or more elongated openings adjacent to the tali targeting opening that can be used to identify the location of a subtalar joint adjacent to the calcaneus, at which point a fixation screw can be advanced through the tali targeting opening into the dense bone of the sustentaculum tali.

The invention in one form is directed to a calcaneal targeting device that includes a guide body configured to target a corresponding calcaneal bone plate. The guide body includes at least one mounting opening that is configured to align with a corresponding mounting opening of the calcaneal bone plate, at least one targeting opening configured to align with a corresponding fixation opening of the calcaneal bone plate, and a guiding portion that includes a tali targeting opening and a first elongated opening that has a first length. The first elongated opening is configured to allow sliding of a guide wire across the first length and align the tali targeting opening with a sustentaculum tali.

The invention in another form is directed to a method of aligning a calcaneal bone plate including a plate tali opening to a calcaneus that includes attaching a calcaneal targeting guide to the calcaneal bone plate such that a tali targeting opening of the calcaneal targeting guide aligns with the plate tali opening. The targeting guide has a first elongated opening with a first length and is sized to allow sliding of a guide wire across the first length. The first elongated opening is adjacent to the tali targeting opening. The attached calcaneal bone plate is positioned on a lateral side of the calcaneus. A guide wire is advanced through the first elongated opening toward the calcaneus. The position of the attached calcaneal bone plate is adjusted so that the guide wire rests within a subtalar joint adjacent to the calcaneus.

An advantage of the present invention is that the targeting guide can allow a surgeon to reliably find an area of dense bone, the sustentaculum tali, that a bone screw can be advanced through to fixate a bone plate.

Another advantage is that the number of fluoroscopic images taken during the surgery can be reduced.

Yet another advantage is that no extra surgical tools are required.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

DETAILED DESCRIPTION OF THE INVENTION

Figure 1:
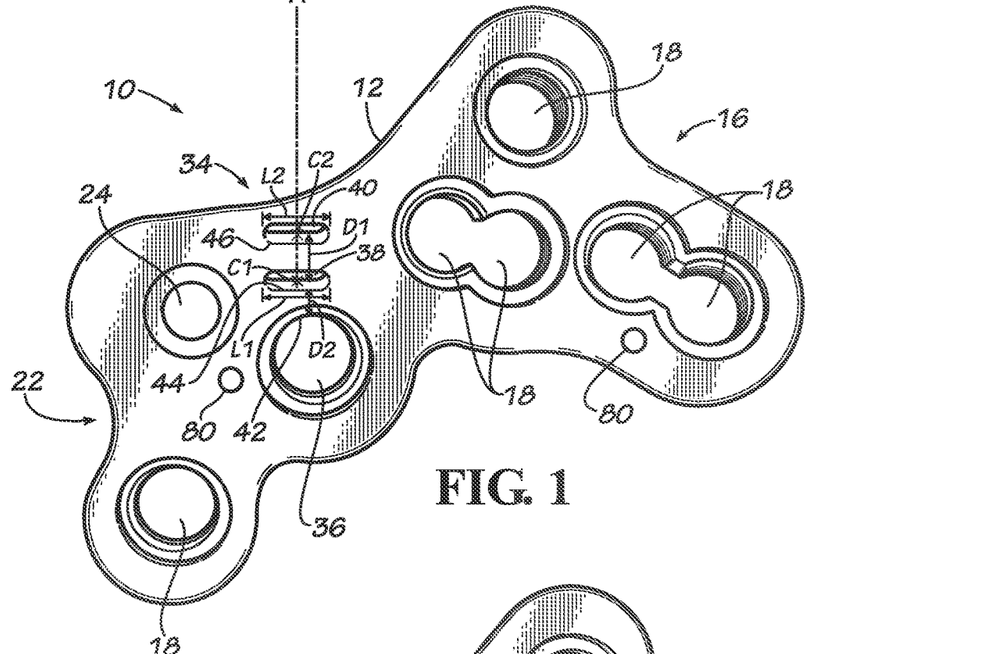
FIG. 1 is a perspective view of an embodiment of a calcaneal targeting guide of the present invention.

Referring now to the drawings, and more particularly to FIG. 1, there is shown a calcaneal targeting device 10, shown as a calcaneal targeting guide, which generally includes a guide body 12 that is sized and shaped to target openings on a corresponding calcaneal bone plate 14 (shown in FIGS. 4-10). While reference to the corresponding calcaneal bone plate 14 is made throughout, it should be understood that a calcaneal targeting guide 10 taught by the present invention could be configured for use with one or more different configurations of calcaneal bone plates and that the calcaneal bone plate shown is merely for reference and not limitation. It is useful, but not necessary, that the guide body 12 is formed out of a radiolucent material. As used herein, "radiolucent material" refers to a material that allows x-rays to pass through in a way that the radiolucent material does not substantially interfere with a fluoroscopic image being developed of an object that is behind the radiolucent material relative to a fluoroscope. Example radiolucent materials include carbon fiber, glass fiber, polymers, or fiber reinforced polymers. It is useful if the guide body 12 comprises a carbon fiber or a fiber reinforced polymer, which can have high strength properties useful for surgical applications.

Figure 2:
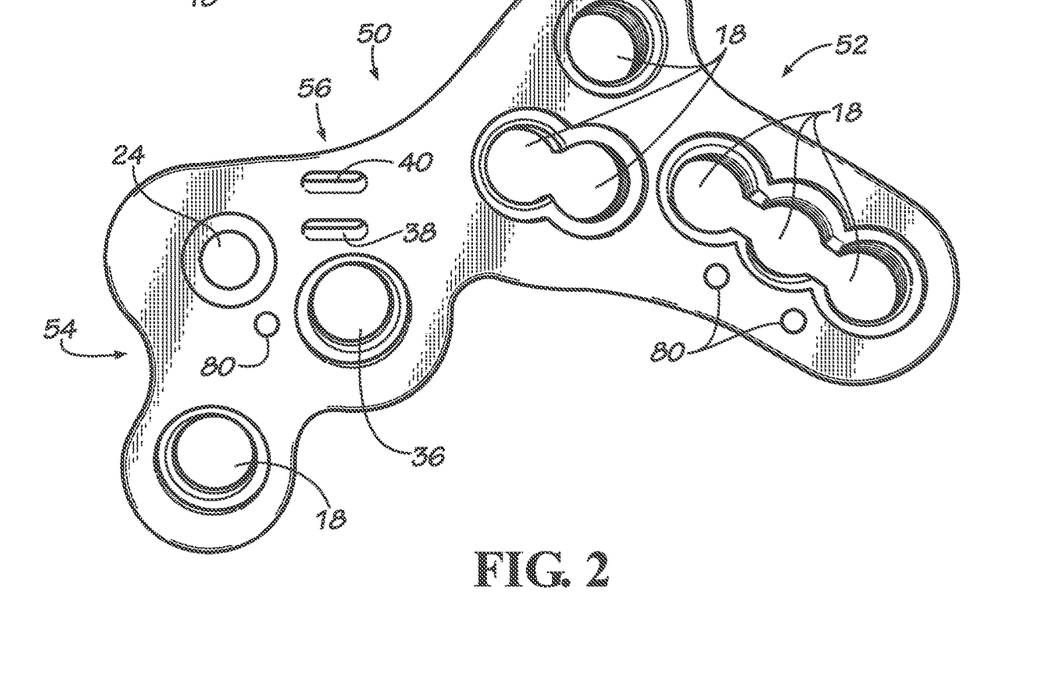
FIG. 2 is a perspective view of another embodiment of a calcaneal targeting guide of the present invention.
Figure 3:
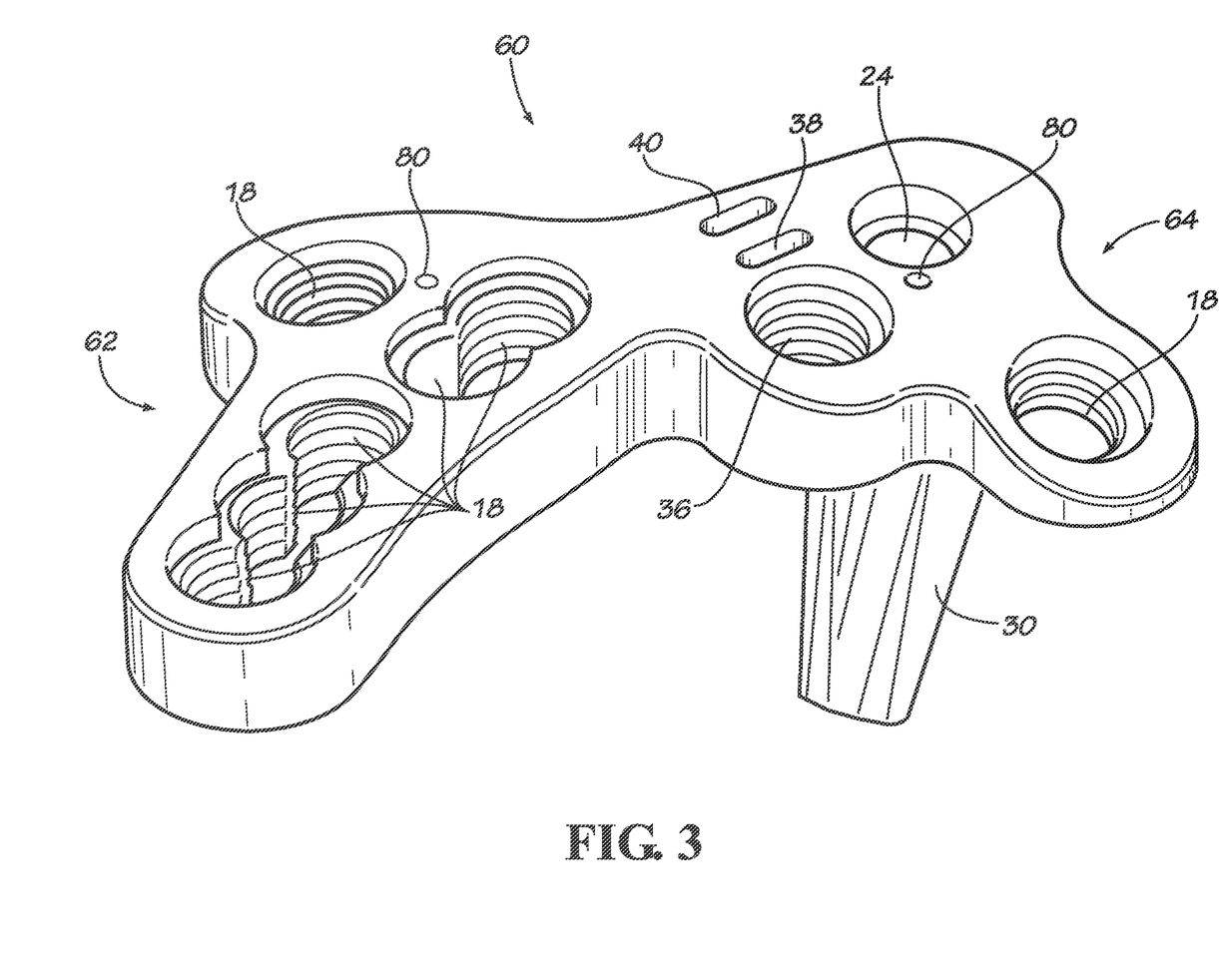
FIG. 3 is a perspective view of yet another embodiment of a calcaneal targeting guide of the present invention.

As shown in FIG. 1, the guide body 12 has a main targeting portion 16 with targeting openings 18 that are formed through the guide body 12 to target corresponding fixation openings 20 of the calcaneal bone plate 14. The targeting guide 10 shown in FIG. 1 has been configured to target a calcaneal bone plate that is implanted on a calcaneus of a patient's left leg, but other targeting guide configurations are also shown in FIGS. 2-3 and described below. While the portion 16 is referred to as a "main targeting portion," it is not the only portion of the targeting guide 10 where targeting openings 18 can be formed, as seen in FIGS. 1-3, and is therefore only called such for convenience in describing where the majority of the targeting openings 18 of the exemplary targeting guide 10 are located. Optionally, a targeting guide that has targeting openings uniformly distributed across the guide body could also be made and used in accordance with the present invention. The targeting openings 18 can be positioned on the guide body 12 as desired so that they line up with their corresponding fixation openings 20 when the targeting guide 10 is attached to the bone plate 14. The targeting openings 18 can be single, substantially circular openings or multiple, substantially circular openings that are connected, as shown in FIGS. 1-3. The targeting openings 18 are shown as being substantially circular or multiple substantially circular openings connected together, but could be formed as other shapes as well. One or more targeting openings 18 can be threaded, as shown, to interact with a tool that is inserted through the targeting opening(s) 18, such as a drill guide, in order to secure the tool within the threaded targeting opening(s) 18. The main targeting portion 16, as shown, has a multi-curvature shape, but the shape can be adjusted as desired to position the targeting openings 18 so that they align with their corresponding fixation openings 20 on the calcaneal bone plate 14. Other parameters that can be considered when choosing the shape of the main targeting portion 16, and guide body 12 in general, can include user preference, ergonomics, target calcaneal bone plate, etc.

The guide body 12 includes a mounting portion 22, which is shown as being on a side of the guide body 12 opposite the main targeting portion 16. The mounting portion 22 includes a mounting opening 24 that is placed on the mounting portion 22 so that it aligns with a corresponding mounting opening 26 of the calcaneal bone plate 14. A mounting member 28, shown in FIGS. 4-9, can be placed through the mounting opening 24 and interact with the corresponding mounting opening 26 to attach the calcaneal targeting guide 10 to the calcaneal bone plate 14. The mounting member 28 can be a single element, such as a threaded screw, or could include multiple pieces, as shown. As can be seen in FIGS. 4-10, the mounting member 28 shown includes a mounting sleeve 30 that extends a desired distance from the mounting opening 24 to the corresponding mounting opening 26. The mounting sleeve 30 can have mounting prongs (not shown) that interact with prong openings (not shown) on the calcaneal bone plate 14. The mounting prongs and prong openings are positioned and shaped in such a way that when the mounting prongs interact with the prong openings, the targeting guide 10 and calcaneal bone plate 14 are properly aligned. A mounting screw (not shown) can then be inserted through the mounting sleeve 30 toward the corresponding mounting opening 26. The mounting screw can have threading at one end that interacts with threading of the corresponding mounting opening 26 to secure the mounting screw to the calcaneal bone plate 14 and threading at an opposite end that interacts with a mounting nut 32 that can be advanced along the mounting screw toward the mounting sleeve 30. When the mounting nut 32 is fully advanced along the mounting screw, the mounting screw is tightly attached to the calcaneal targeting guide 10. When the mounting screw is attached to both the calcaneal targeting guide 10 and calcaneal bone plate 14, the targeting guide 10 and bone plate 14 are attached and should be properly aligned. The previously described mounting portion 22 and way to attach the calcaneal targeting guide 10 to the calcaneal bone plate 14 are given only as an example of how the targeting guide 10 can be attached to the bone plate 14 and not meant to limit the configuration(s) that the mounting portion 22 can assume.

The guide body 12 further includes a guiding portion 34 that can be located between the main targeting portion 16 and mounting portion 22. Depending on the configuration of the corresponding calcaneal bone plate 14, the guiding portion 34 can have other relative locations on the guide body 12. The guiding portion 34 includes a tali targeting opening 36 and one or more elongated openings 38, 40 that are located adjacent to the tali targeting opening 36. The guiding portion 34 is shown as having two elongated openings 38 and 40, but the guiding portion 34 could be configured to have only one elongated opening or more than two elongated openings, if desired. When the tali targeting opening 36 has a circular shape, as shown, the tali targeting opening 36 has a circumferential edge 42 that defines an outer boundary of the tali targeting opening 36. If the tali targeting opening 36 is not shaped as a circular opening, the circumferential edge 42 can be referred to as a peripheral edge. The size of the tali targeting opening 36 can be adjusted, as desired, to allow for the passage of differently sized medical devices, such as orthopaedic screws, through the tali targeting opening 36. Each elongated opening 38, 40 has a respective center C1 and C2, length L1 and L2, and elongated edge 44 and 46. The elongated openings 38 and 40 are sized so that a guide wire 48 (shown in FIGS. 4-7) can be inserted through the elongated openings 38 and 40 and slide across the lengths L1 and L2. The elongated openings 38 and 40, as shown, have substantially identical shapes, but this is not necessary. Particularly, the lengths L1 and L2 can be adjusted to give differing amounts of sliding that the calcaneal targeting guide 10 can take along the guide wire 48, which will be described below. As can be seen, the elongated openings 38 and 40 have respective centers C1 and C2 that are aligned on a centering axis A. In this respect, the elongated openings 38 and 40 have similar orientations relative to the tali targeting opening 36, with the difference being a size adjusting distance D1 between the centers C1 and C2 of elongated openings 38 and 40. The size adjusting distance D1 allows for proper guidance of the calcaneal targeting guide 10 relative to a patient's calcaneus, with adjustment being possible for patients with differing anatomical sizes, which will be described below. Useful values for the size adjusting distance D1 have been found to be between about 2 mm and 12 mm, but other similar values can be chosen to account for the size difference between calcaneus bones of different patients. As shown, the size adjusting distance D1 of the shown calcaneal targeting guide 10 is about 5 mm. While shown, it is not required that the elongated openings 38 and 40 are aligned on the centering axis A. There is also an alignment distance D2 between the elongated edge 44 and circumferential edge 42. The alignment distance D2 is the minimum distance between the tali targeting opening 36 and elongated opening 38, which can be adjusted to account for relative distance differences between a patient's subtalar joint and sustentaculum tali, which will be described below. Useful values for the alignment distance D2 can be similar to those of the size adjusting distance, between about 2 mm and 12 mm, but can also be adjusted to account for differences in patient anatomies, which will be described more fully below. It should therefore be appreciated that the relative distances between the tali targeting opening 36 and elongated opening(s) 38, 40 can be adjusted to account for differing patient anatomies, and the present invention contemplates many different types of adjustments for the relative distances so that a calcaneal targeting guide can be produced that is either for general use or tailored to a specific patient or group of patients.

Referring now to FIG. 2, another embodiment of a calcaneal targeting guide 50 is shown. The calcaneal targeting guide 50 is similar to the calcaneal targeting guide 10 shown and includes a main targeting portion 52, a mounting portion 54 and a guiding portion 56. As can be seen, the main difference between targeting guide 50 and targeting guide 10 is that the main targeting portion 52 of targeting guide 50 is larger than the main targeting portion 16 of targeting guide 10. Specifically, the main targeting portion 52 includes three connected targeting openings 18, as opposed to the main targeting portion 16 which includes two connected targeting openings 18. In this regard, the main targeting portion 52 allows for targeting more corresponding fixation openings on a calcaneal bone plate (not shown) than the main targeting portion 16, which can be utilized either due to a difference in patient size or fracture pattern. It can therefore be appreciated that the size and configuration of a calcaneal targeting guide of the present invention can be adjusted to correspond to differing patient anatomies, fracture patterns and calcaneal bone plates used.

Referring now to FIG. 3, another embodiment of a calcaneal targeting guide 60 is shown. The calcaneal targeting guide 60 includes a main targeting portion 62, mounting portion 64 and guiding portion 66. As can be seen, the targeting guide 60 is substantially identical to the targeting guide 50 shown in FIG. 2, but is a mirror of the targeting guide 50. In this respect, the targeting guide 60 is configured to be used on a calcaneus of a right leg, as opposed to the targeting guide 10 which is configured to be used on a calcaneus of a left leg. It can therefore be appreciated that the configuration of a calcaneal targeting guide of the present invention can be adjusted to be used in either right leg or left leg applications with relative ease.

Referring now to FIGS. 4-10, a method of aligning and fixating a calcaneal bone plate 14 on a calcaneus bone B1 using the targeting guide 10 in a sinus tarsi approach is shown. It should be appreciated that while targeting guide 10 is shown being used in conjunction with calcaneal bone plate 14, other targeting guides, such as targeting guides 50 and 60, and calcaneal bone plates can also be used in accordance with the present invention. To begin, an incision is made by the surgeon on a lateral side of the calcaneus B1 that is of sufficient size to allow the bone plate 14 to be placed against the lateral side of the calcaneus B1. The bone plate 14 is attached to and aligned with the targeting guide 10, as previously described, and placed against the lateral side of the calcaneus B1. Once the bone plate 14 is contacting the calcaneus B1, a guide wire 48 can be advanced through elongated opening 38 or 40 toward the calcaneus B1.

Figure 4:
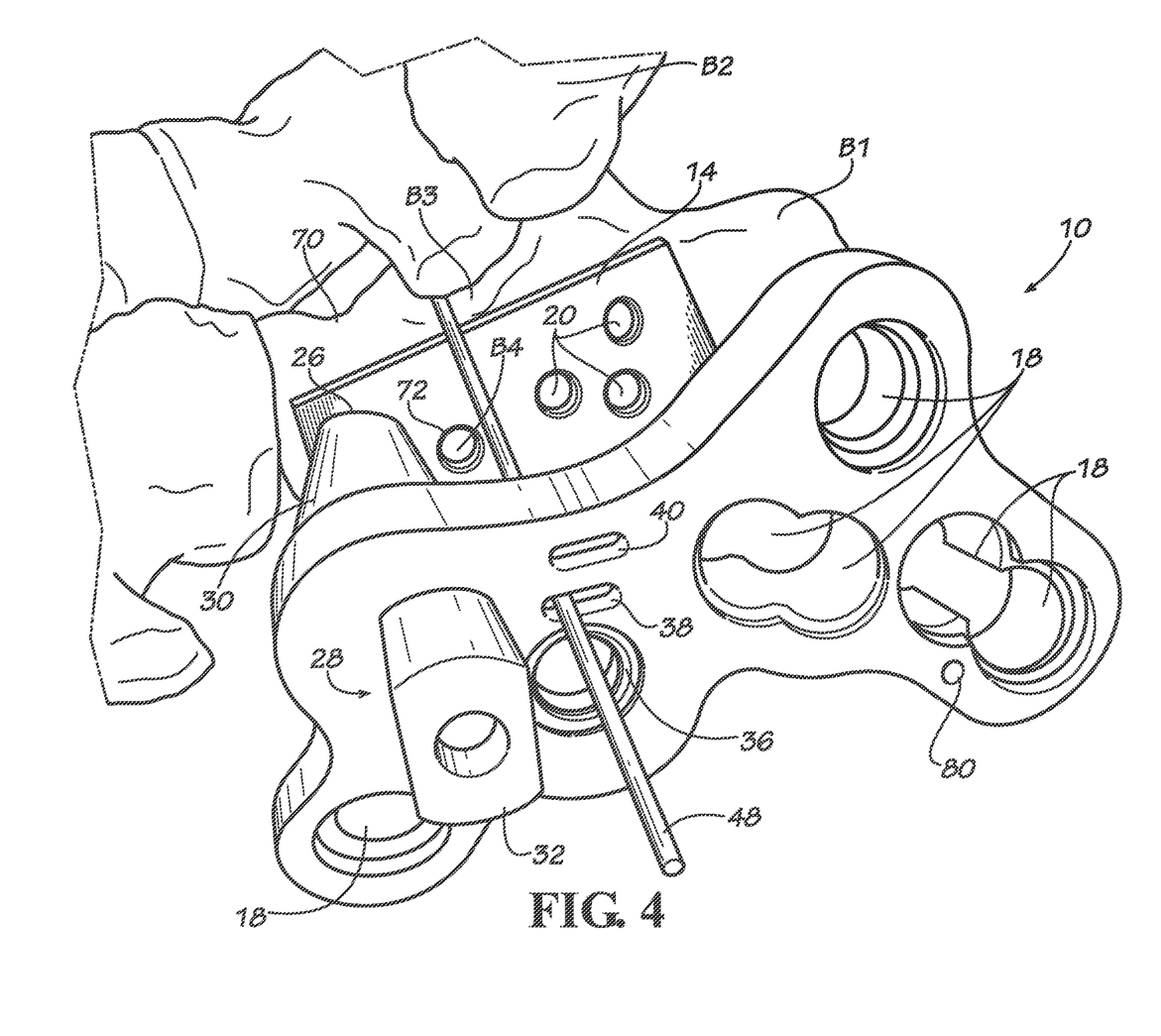
FIG. 4 is a perspective view of a method of using the calcaneal targeting guide shown in FIG. 1 to align and fixate a calcaneal bone plate to a calcaneus according to the present invention.

To align the calcaneal bone plate 14 and ensure that a fixation opening 20 of the bone plate 14 is aligned with an area of dense bone, the guide wire 48 is adjusted along a top surface 70 of the calcaneus B1 until the guide wire 48 rests between a talus bone B2 and the calcaneus B1 in a subtalar joint B3, as shown in FIG. 4. To adjust the guide wire's 48 position, the guide wire 48 can either be slid along the length L1 or L2, depending on which elongated opening 38 or 40 the guide wire 48 is held in, until the guide wire 48 rests within the subtalar joint B3 or the targeting guide 10 and attached bone plate's 14 position can be adjusted until the guide wire 48 rests within the subtalar joint B3. If the surgeon is holding the guide wire 48, the surgeon will be able to feel a tactile feedback when the guide wire 48 transitions from sliding across the top surface 70 of the calcaneus B1 to residing within the subtalar joint B3. This tactile feedback allows the surgeon to approximately know that the guide wire 48 is properly placed, which can be verified by taking a fluoroscopic image of the area or adjusted based on a fluoroscopic image.

Once the guide wire 48 is properly placed and resting within the subtalar joint B3, the bone plate 14 should have at least one fixation opening 72, hereafter referred to as a plate tali opening, that is aligned with a sustentaculum tali B4 of the calcaneus B1, which provides an area of dense bone for fixation. If the guide wire 48 is held within elongated opening 40 rather than elongated opening 38 and resting within the subtalar joint B3, the plate tali opening 72 will be farther from the subtalar joint B3 by a distance that is equal to the size adjusting distance D1 than if the guide wire 48 is held within elongated opening 38. In this regard, the adjusting distance D1 and alignment distance D2 can be chosen, as desired, so that the plate tali opening 72 will align with the sustentaculum tali B4 when the guide wire 48 rests within the subtalar joint B3. The previously described adjusting distance D1 and alignment distance D2 values allow for such placement. By using the guiding portion 34 of the targeting guide 10, the bone plate 14 can be fixated in the dense bone of the sustentaculum tali B4 without violating the subtalar joint B3. Elongated opening 38, which aligns the plate tali opening 72 closer to the subtalar joint B3, can be used to align the bone plate 14 when the patient has a shorter distance between the subtalar joint B3 and sustentaculum tali B4, whereas elongated opening 40 can be used when the patient has a larger distance between the subtalar joint B3 and sustentaculum tali B4.

Figure 5:
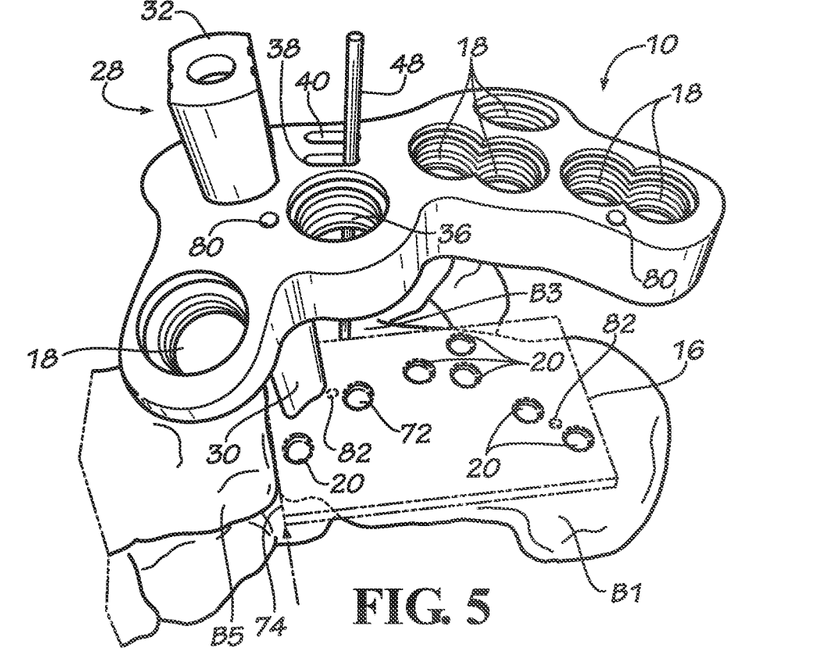
FIG. 5 is a further step of the method shown in FIG. 4.
Figure 6:
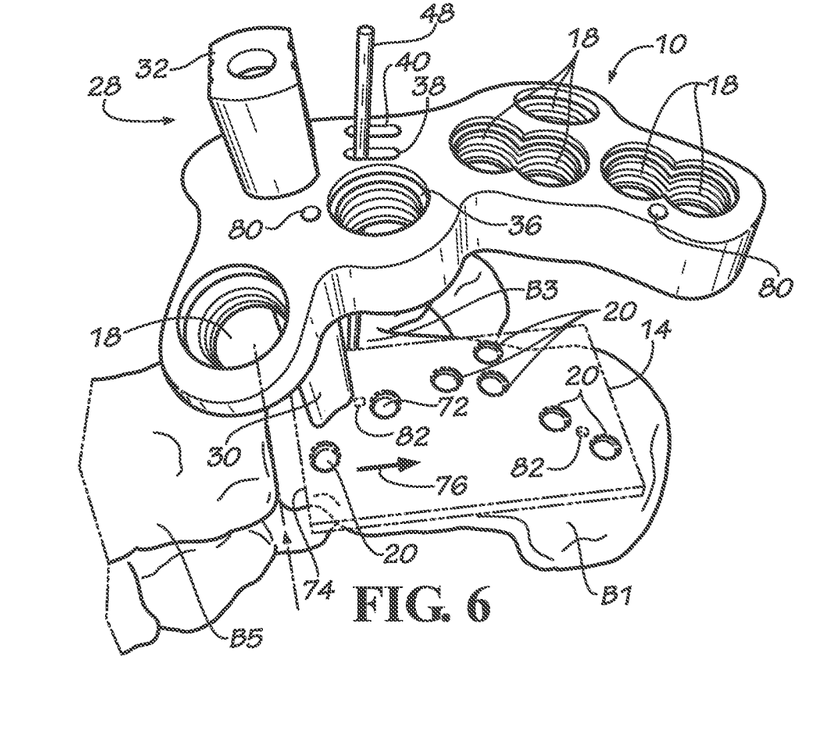
FIG. 6 is a further step of the method shown in FIGS. 4 and 5.

Once the bone plate 14 has been properly aligned relative to the subtalar joint B3, the position of the bone plate 14 might need to be adjusted, as shown in FIG. 5, so that an anterior aspect 74 of the bone plate 14 is just posterior to the calcaneocuboid joint B5, as shown in FIG. 6. To achieve this positioning, the guide wire 48 can be held in place and the targeting guide 10 can slide its elongated opening 38 (or elongated opening 40) across the guide wire 48, as indicated by an arrow 76 in FIG. 6. A marked line in FIG. 5 shows the location of the anterior aspect 74 of the bone plate 14, and a similar marked line in FIG. 6 shows the same location after the bone plate 14 has been moved. By sliding the targeting guide 10 across the guide wire 48 using the elongated opening 38, the positioning of the bone plate 14 relative to the subtalar joint B3 can be maintained while allowing for the bone plate 14 to be anteriorly distanced away from or posteriorly placed toward the calcaneocuboid joint B5.

Figure 7:
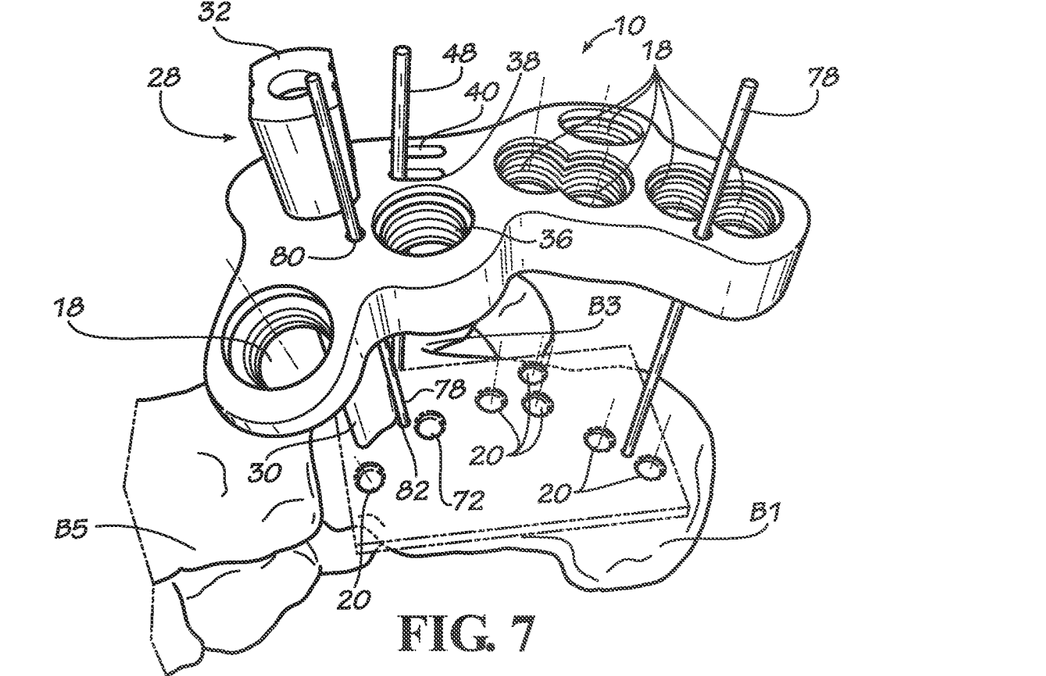
FIG. 7 is a further step of the method shown in FIGS. 4-6.

Once the bone plate 14 has been properly distanced from the calcaneocuboid joint B5, as shown in FIG. 7, the bone plate 14 can be fixated to the calcaneus B1. To help with this fixation, additional guide wires 78 can be inserted through wire openings 80 formed through the guide body 12 that align with corresponding wire openings 82 of the bone plate 14. The additional guide wires 78 provide additional temporary fixation of the bone plate 14 in the proper position before more permanent fixation to the calcaneus B1 is complete. This step is not necessary, but may be useful if the surgeon is concerned with losing the proper positioning of the bone plate 14 relative to the sustentaculum tali B4.

Figure 8:
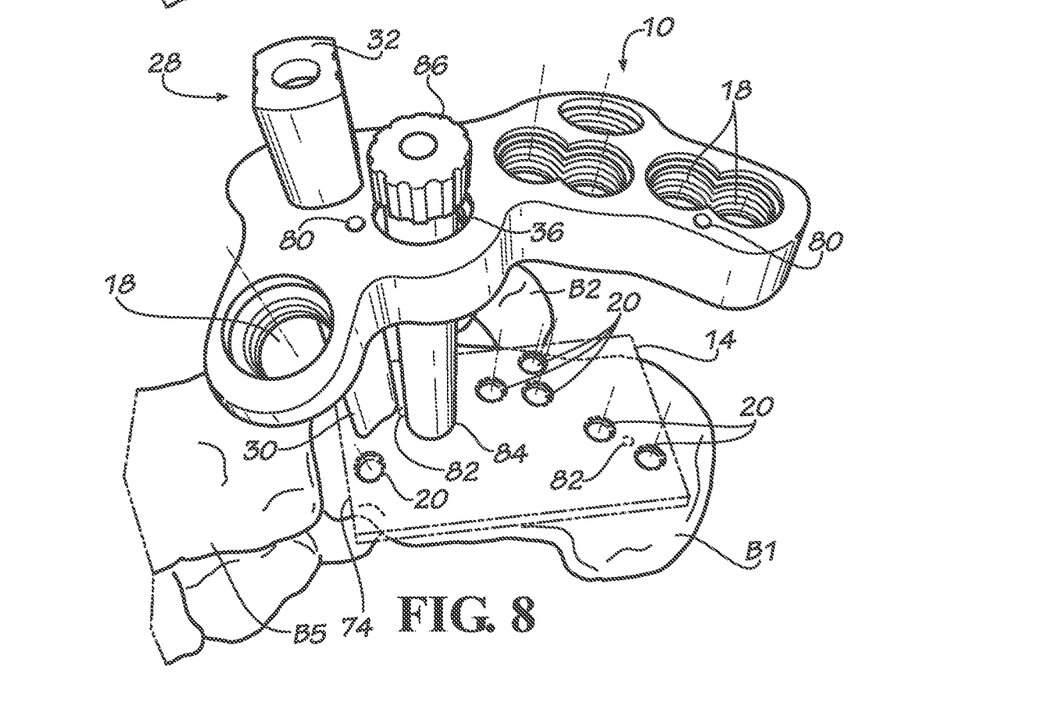
FIG. 8 is a further step of the method shown in FIGS. 4-7.

Referring now to FIG. 8, it can be seen that a soft tissue guide 84 holding an attached trocar 86 has been inserted through the tali targeting opening 36. The soft tissue guide 84 and trocar 86 together are advanced percutaneously toward the calcaneus B1 so that an opening 88 of the soft tissue guide 84 is directly above the plate tali opening 72. After placement, the tip of the trocar 86 will be contacting the bone, but the soft tissue guide 84 will not be attached to the bone plate 14. Rather, the soft tissue guide 84 interacts with the tali targeting opening 36 to connect to the targeting guide 10.

Figure 9:
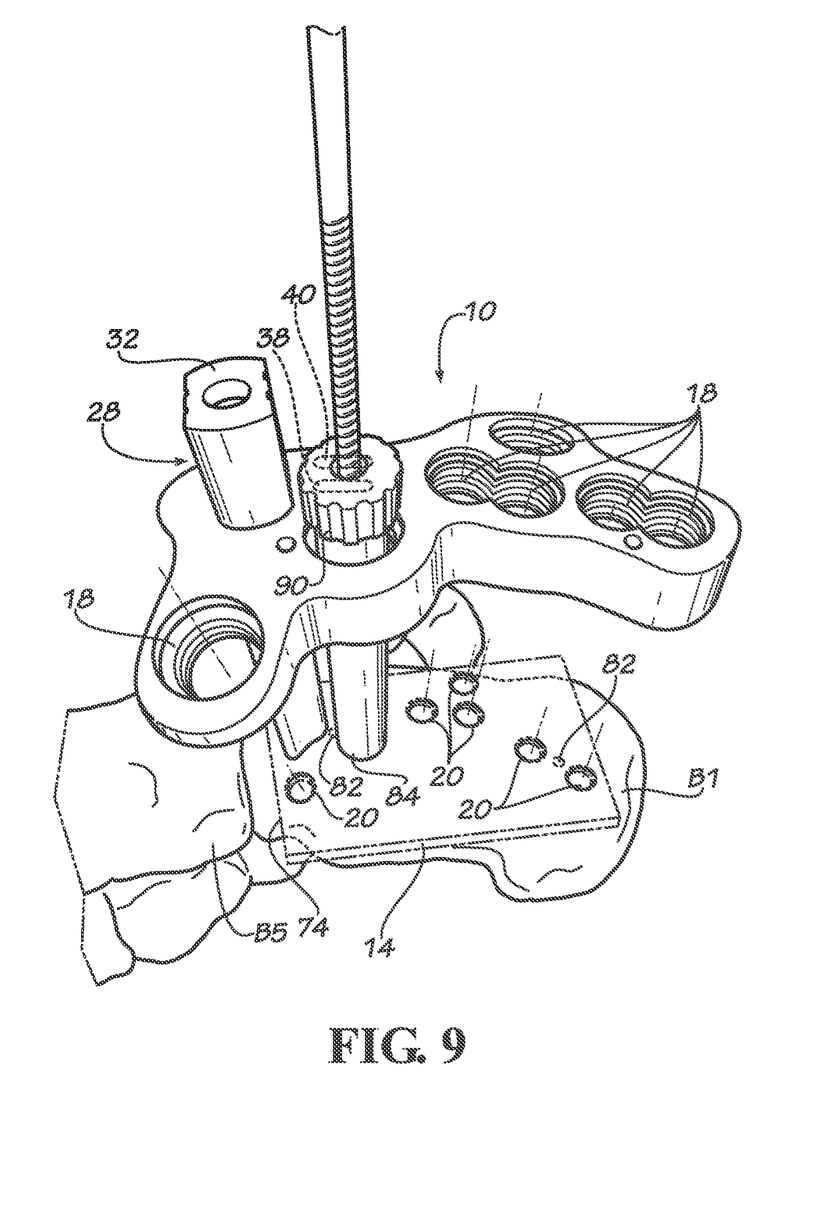
FIG. 9 is a further step of the method shown in FIGS. 4-8.
Figure 10:
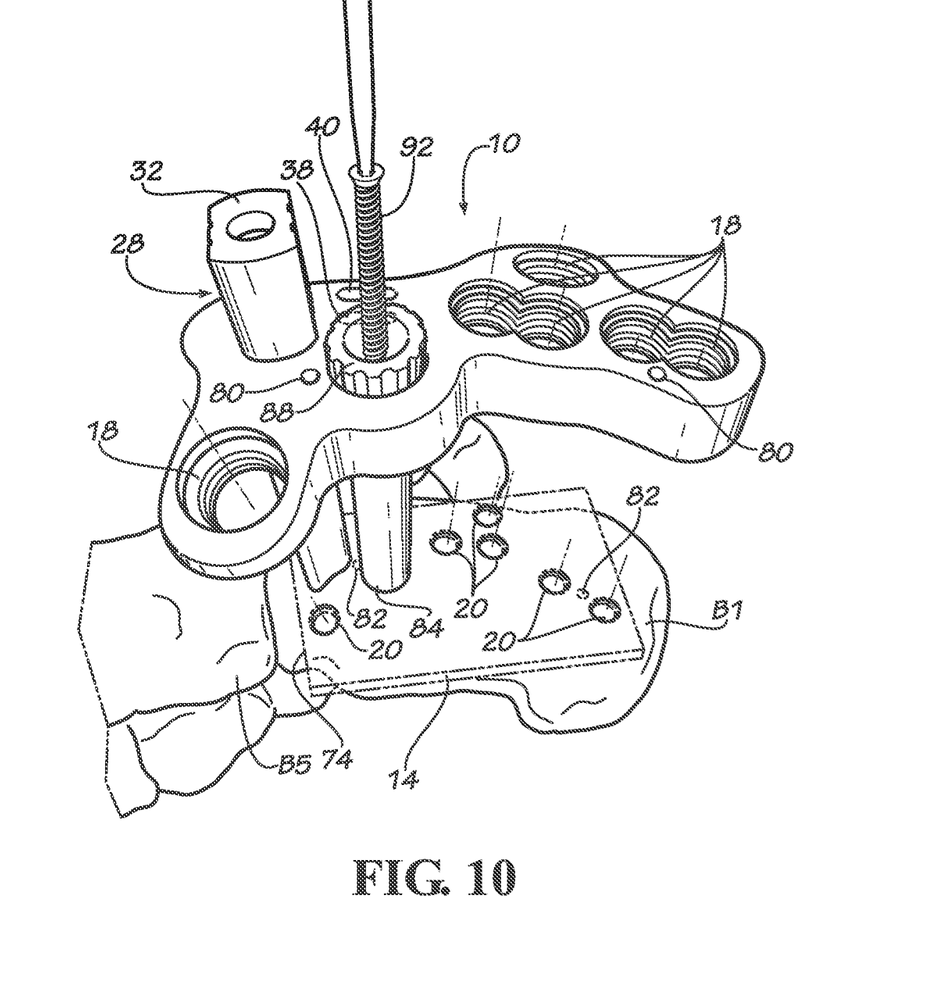
FIG. 10 is a further step of the method shown in FIGS. 4-9.

After the soft tissue guide 84 is in place, as shown in FIGS. 9 and 10, the trocar 86 is removed from the soft tissue guide 84 and replaced with a threaded drill guide 90, as shown in FIG. 9. The threaded drill guide 90 has threading (not shown) that interacts with threading (not shown) of the plate tali opening 72 so that the threaded drill guide 90 is connected to the bone plate 14 at the plate tali opening 72. A reference hole can be drilled into the sustentaculum tali B4 to a depth where an orthopaedic screw 92, shown as a bone screw in FIG. 10, will be seated. As shown in FIG. 10, the threaded drill guide 90 can be removed after making the reference hole and the bone screw 92 can then be advanced through the opening 88 of the soft tissue guide 84. Since the opening 88 is aligned with the plate tali opening 72, which is aligned with sustentaculum tali B4, the bone screw 92 will advance through the plate tali opening 72 into the sustentaculum tali B4 and compress the bone plate 14 against the calcaneus B1. The soft tissue guide 84 can then be removed and additional bone screws (not shown) can be inserted through targeting openings 18 of the targeting guide 10 into other fixation openings 20 of the bone plate 14 to secure fragments and the bone plate 14 to the calcaneus B1.

It can therefore be seen that the present invention provides calcaneal targeting guides 10, 50 and 60 that can be used to fixate a bone plate to a calcaneus in a way that reliably places a fixation screw within the sustentaculum tali and avoids violating the subtalar joint by finding the subtalar joint using one or more elongated openings of the targeting guides 10, 50 and 60. Once the subtalar joint is found using the elongated opening(s), a tali targeting opening of the targeting guide that is adjacent to the elongated opening(s) should be properly distanced from the subtalar joint such that the tali targeting opening is aligned with the sustentaculum tali of the calcaneus. The targeting guide can then be used to fixate the bone plate to the calcaneus, with one of the fixation screws being located within the sustentaculum tali.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A calcaneal targeting system, comprising:
a guide body configured to target a calcaneal bone plate, the guide body having a bottom surface facing the calcaneal bone plate and a top surface opposite the bottom surface, the guide body including:
at least one mounting opening extending from the top surface to the bottom surface and configured to align with a corresponding mounting opening of the calcaneal bone plate;
at least one targeting opening extending from the top surface to the bottom surface and configured to align with a corresponding fixation opening of the calcaneal bone plate, at least one of the at least one targeting opening having an elongated shape and including a plurality of substantially circular openings that overlap each other at the top surface and at the bottom surface; and
a guiding portion that includes a tali targeting opening and first and second elongated openings adjacent the tali targeting opening, each of the first and second elongated openings having a length and two opposing elongate edges extending from the top surface to the bottom surface, the two opposing elongate edges being spaced apart by a uniform width, each of the first and second elongated openings configured to allow sliding of a guide wire across the first length to locate a subtalar joint and align the tali targeting opening with a sustentaculum tali; and
a mounting sleeve configured to extend from the bottom surface from the at least one mounting opening to the corresponding mounting opening of the calcaneal bone plate and adapted to space apart the guide body and the calcaneal bone plate;
wherein the second elongated opening is distinct from and parallel to the first elongated opening, and no intervening openings being defined in the guide body between the first and second elongated openings; and
wherein the first elongated opening has a first center and the second elongated opening has a second center, the first center and the second center being substantially aligned along a centering axis.

2. The calcaneal targeting system of claim 1, wherein the first center and the second center have a size adjusting distance therebetween.

3. The calcaneal targeting system of claim 2, wherein the size adjusting distance is between 2 mm and 12 mm.

4. The calcaneal targeting system of claim 3, wherein the size adjusting distance is about 5 mm.

5. The calcaneal targeting system of claim 1, wherein the second elongated opening has a substantially identical shape to the first elongated opening.

6. The calcaneal targeting system of claim 1, wherein:
the first elongated opening has a first elongated edge, the first elongated edge being one of the two opposing elongate edges; and
the tali targeting opening has a circumferential edge, the circumferential edge having an alignment distance from the first elongated edge.

7. The calcaneal targeting system of claim 6, wherein the alignment distance is between 2 mm and 12 mm.

8. The calcaneal targeting system of claim 7, wherein the alignment distance is about 5 mm.

9. The calcaneal targeting system of claim 1, wherein the guide body comprises a substantially radiolucent material.

10. The calcaneal targeting system of claim 1, wherein the mounting sleeve has an interior configured to accommodate a mounting screw that is adapted to be threadably attached to the calcaneal bone plate.

11. The calcaneal targeting system of claim 10, wherein the mounting screw has a threading at a first end that interacts with a threading of the corresponding mounting opening of the calcaneal bone plate to attach the mounting screw to the calcaneal bone plate.

12. The calcaneal targeting system of claim 11, wherein the mounting screw has a threading at a second end, opposite the first end, configured to interact with a threading of a mounting nut that is advanceable along the mounting screw toward the mounting sleeve.

13. The calcaneal targeting system of claim 12, wherein when the mounting nut is fully advanced along the mounting screw, the mounting screw is attached to the guide body.

14. The calcaneal targeting system of claim 1, wherein at least one of the at least one targeting opening comprises a plurality of substantially circular openings that overlap to form an irregular shape.

15. The calcaneal targeting system of claim 1, wherein the first elongated opening in the guiding portion does not correspond to any opening of the calcaneal bone plate.

16. A calcaneal targeting system, comprising:
a guide body configured to target a calcaneal bone plate, the guide body having a bottom surface facing the calcaneal bone plate and a top surface opposite the bottom surface, the guide body including:
at least one mounting opening extending from the top surface to the bottom surface and configured to align with a corresponding mounting opening of the calcaneal bone plate;
at least one targeting opening extending from the top surface to the bottom surface and configured to align with a corresponding fixation opening of the calcaneal bone plate, at least one of the at least one targeting opening having an elongated shape and including a plurality of substantially circular openings that overlap each other at the top surface and at the bottom surface; and
a guiding portion that includes a tali targeting opening and first and second elongated openings adjacent the tali targeting opening, each of the first and second elongated openings having a length and two opposing elongate edges extending from the top surface to the bottom surface, the two opposing elongate edges being spaced apart by a uniform width, each of the first and second elongated openings configured to allow sliding of a guide wire across the length to locate a subtalar joint and align the tali targeting opening with a sustentaculum tali,
wherein the first elongated opening in the guiding portion does not correspond to any opening of the calcaneal bone plate; and
a mounting sleeve configured to extend from the bottom surface from the at least one mounting opening to the corresponding mounting opening of the calcaneal bone plate and adapted to space apart the guide body and the calcaneal bone plate; and
wherein the second elongated opening is distinct from and parallel to the first elongated opening, and no intervening openings being defined in the guide body between the first and second elongated openings; and
wherein the first elongated opening has a first center and the second elongated opening has a second center, the first center and the second center being substantially aligned along a centering axis.

17. The calcaneal targeting system of claim 16, wherein:
the mounting sleeve has an interior configured to accommodate a mounting screw that is adapted to be threadably attached to the calcaneal bone plate;
the mounting screw has a threading at a first end that interacts with a threading of the corresponding mounting opening of the calcaneal bone plate to attach the mounting screw to the calcaneal bone plate;
the mounting screw has a threading at a second end, opposite the first end, configured to interact with a threading of a mounting nut that is advanceable along the mounting screw toward the mounting sleeve; and
when the mounting nut is fully advanced along the mounting screw, the mounting screw is attached to the guide body.

18. A calcaneal targeting system, comprising:
a guide body configured to target a calcaneal bone plate, the guide body having a bottom surface facing the calcaneal bone plate and a top surface opposite the bottom surface, the guide body including:
at least one mounting opening extending from the top surface to the bottom surface and configured to align with a corresponding mounting opening of the calcaneal bone plate;
at least one targeting opening extending from the top surface to the bottom surface and configured to align with a corresponding fixation opening of the calcaneal bone plate, at least one of the at least one targeting opening having an elongated shape and including a plurality of substantially circular openings that overlap each other to form an irregular shape at the top surface and at the bottom surface; and
a guiding portion that includes a tali targeting opening and first and second elongated openings adjacent the tali targeting opening, each of the first and second elongated openings having a length and two opposing elongate edges extending from the top surface to the bottom surface, the two opposing elongate edges being spaced apart by a uniform width, each of the first and second elongated openings configured to allow sliding of a guide wire across the length to locate a subtalar joint and align the tali targeting opening with a sustentaculum tali; and a mounting sleeve configured to extend from the bottom surface from the at least one mounting opening to the corresponding mounting opening of the calcaneal bone plate and adapted to space apart the guide body and the calcaneal bone plate, the mounting sleeve having an interior configured to accommodate a mounting screw that is adapted to be threadably attached to the calcaneal bone plate, the mounting screw having a threading at a first end that interacts with a threading of the corresponding mounting opening of the calcaneal bone plate to attach the mounting screw to the calcaneal bone plate, the mounting screw having a threading at a second end, opposite the first end, configured to interact with a threading of a mounting nut that is advanceable along the mounting screw toward the mounting sleeve, wherein when the mounting nut is fully advanced along the mounting screw, the mounting screw is attached to the guide body; and wherein the second elongated opening is distinct from and parallel to the first elongated opening, and no intervening openings being defined in the guide body between the first and second elongated openings; and wherein the first elongated opening has a first center and the second elongated opening has a second center, the first center and the second center being substantially aligned along a centering axis.

* * * * *